United States Patent [19]

Eckhardt et al.

[11] Patent Number: 4,532,337

[45] Date of Patent: Jul. 30, 1985

[54] PREPARATION OF 3-FORMYL-5,6-DIHYDRO-2H-PYRAN

[75] Inventors: Heinz Eckhardt, Ludwigshafen; Klaus Halbritter, Mannheim; Norbert Goetz, Worms; Gerd Heilen, Speyer, all of Fed. Rep. of Germany

[73] Assignee: BASF Aktiengesellschaft, Ludwigshafen, Fed. Rep. of Germany

[21] Appl. No.: 584,334

[22] Filed: Feb. 28, 1984

[51] Int. Cl.$^3$ ............................................. C07D 309/00
[52] U.S. Cl. .................................................. 549/425
[58] Field of Search ......................................... 549/425

[56] References Cited

U.S. PATENT DOCUMENTS

| | | | |
|---|---|---|---|
| 2,479,283 | 8/1949 | Whetstone | 549/425 |
| 2,479,284 | 8/1949 | Whetstone | 549/425 |
| 2,514,156 | 7/1950 | Geyer et al. | 549/425 |
| 2,537,579 | 8/1949 | Fountain et al. | 549/201 |
| 3,159,651 | 12/1964 | Johnson et al. | 549/425 |

OTHER PUBLICATIONS

C. W. Smith, Acrolein, (Heidelberg 1975).

Primary Examiner—Ethel G. Love
Attorney, Agent, or Firm—John H. Shurtleff

[57] ABSTRACT

3-Formyl-5,6-dihydro-2H-pyran is prepared by conversion of acrolein in the presence of water, acids and halohydrocarbons of 1 to 6 carbon atoms and 1 to 6 halogen atoms as solvents at from 60° to 150° C. The 3-formyl-5,6-dihydro-2H-pyran obtained by the novel process is a valuable starting material for the preparation of dyes and crop protection agents.

9 Claims, No Drawings

PREPARATION OF 3-FORMYL-5,6-DIHYDRO-2H-PYRAN

The present invention relates to a process for the preparation of 3-formyl-5,6-dihydro-2H-pyran by conversion of acrolein in the presence of water, acids and halohydrocarbons of 1 to 6 carbon atoms and 1 to 6 halogen atoms as solvents at between 60° and 150° C.

U.S. Pat. No. 2,514,156 describes the conversion of acrolein in the presence of aqueous hydrochloric acid and toluene, preferably at 40°–70° C. (Example 1), which gives a yield of 32% of 3-formyl-5,6-dihydro-2H-pyran. It states explicitly that the use of higher reaction temperatures gives poorer results (column 3, lines 16 to 33) and that the use of inert solvents does not affect the outcome but merely facilitates control of the reaction temperature (column 3, lines 44 to 51). In addition to toluene, benzene is mentioned.

C. W. Smith, Acrolein (Heidelberg, 1975) describes a conversion of acrolein at 170° C. in the presence of benzene, furan or diethyl ether, without added acid, giving a 40–45% yield of 3,4-dihydro-2(H)-pyran-2-carboxaldehyde (loc. cit., page 168, paragraph 1). The publication points out that the organic solvents are used solely to prevent carbonization and that good yields are achieved in the absence of solvents. Moreover, it is known (loc. cit., top of page 199, page 201, 3rd paragraph) that an addition reaction between unsaturated compounds and acrolein requires relatively high temperatures, namely from 150° to 200° C. The publication moreover mentions (loc. cit., page 140) a conversion of acrolein at 70° C. in the presence of aqueous phosphoric acid and benzene, used for the preparation of 3-formyl-5,6-dihydro-2H-pyran. Under these conditions, the reaction is incomplete since the benzene phase must repeatedly be separated off and distilled and on each pass the unconverted acrolein together with the benzene has to be recycled to the reaction vessel. In this way, a total yield of 58% is achieved in a total reaction time of 10 hours. Given the toxicological properties of benzene and acrolein, such lengthy manipulation of these substances is disadvantageous, especially on an industrial scale, in respect of simple and economical operation, operating safety and protection of the environment.

We have found that 3-formyl-5,6-dihydro-2H-pyran of the formula

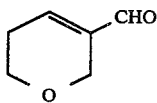

is obtained in an advantageous manner by conversion of acrolein in the presence of water, acids and organic solvents, at an elevated temperature, if the reaction is carried out in the presence of halohydrocarbons of 1 to 6 carbon atoms and 1 to 6 halogen atoms as solvents, at between 60° and 150° C.

The reaction can be represented by the following equation:

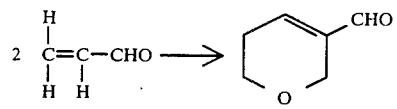

Compared to the conventional processes, the process according to the invention gives 3-formyl-5,6-dihydro-2H-pyran more simply and more economically, with better space-time yield and, in most cases, better yield and greater purity. Lengthy reaction times and numerous working-up steps using benzene are avoided; the process according to the invention is therefore more advantageous in respect of operator safety, operational reliability, saving of working-up equipment, reduced operational control requirements and less environmental pollution.

All these advantageous results of the process according to the invention are surprising in the light of the prior art. It was not to be expected that the use of a particular solvent would significantly influence the yield of end product. It is also surprising that it is not ethers or aromatic hydrocarbons, but specifically the group of halohydrocarbons used according to the invention, which gives advantageous results. It was also not to be expected, in view of the publication by Smith (loc. cit.) that specifically the temperature range according to the invention would be advantageous for the reaction, and in view of the U.S. patent cited it was surprising that temperatures above 70° C. also give advantageous results.

The conversion is carried out at between 60° and 150° C., preferably between 60° and 120° C., especially between 70° and 120° C., under superatmospheric pressure, reduced pressure or, advantageously, atmospheric pressure, continuously or batchwise.

The water is advantageously used in an amount of from 100 to 1,000, preferably from 100 to 500, % by weight based on acrolein. The water and acid can be added separately or as a mixture to the starting charge. Advantageously, an aqueous acid solution is prepared from an appropriate proportion of the water and the remainder of the water is added separately to the starting charge.

The organic solvents used are as a rule cycloaliphatic, aromatic or preferably aliphatic, unsaturated or preferably saturated, halohydrocarbons, advantageously bromohydrocarbons or preferably chlorohydrocarbons, of 1 to 6, preferably 1 to 4, carbon atoms and 1 to 6, preferably 1 to 4, halogen atoms. Suitable halohydrocarbons include amyl chloride, cyclohexyl chloride, dichlorobutanes, isopropyl bromide, n-propyl bromide, butyl bromide, ethyl iodide, propyl iodide, pentachloroethane, 1,1-dichloroethane, n-propyl chloride, 1,2-cis-dichloroethylene, n-butyl chloride, 2-, 3- or iso-butyl chloride, fluorobenzene, bromobenzene, iodobenzene, o-, p- and m-dichlorobenzene, o-, p-, m-dibromobenzene, 1,2,4-trichlorobenzene and 1,4-dibromobutane; advantageous halohydrocarbons are chloroform, carbon tetrachloride, 1,1,1,2-tetrachloroethane, 1,1,2,2-tetrachloroethane, 1,1-, 1,2-, 1,3- and 2,2-dichloropropane, trichloropropane, tetrachloroethylene and chlorobenzene; preferred halohydrocarbons are methylene chloride, 1,2-dichloroethane, 1,1,1- and 1,1,2-trichloroethane and trichloroethylene; mixtures of the above may also be used. Advantageously, the solvent is used in an amount of not less than 10% by volume, preferably from 10 to 200% by volume, or especially from 10 to 100% by volume and very particularly from 20 to 80% by volume, based on the volume of water.

The reaction is carried out in the presence of an acid as the catalyst, advantageously in an amount of from 0.01 to 10, especially from 0.1 to 3, equivalents of acid per mole of acrolein. Organic or more particularly inorganic acids may be used. In place of monobasic acids, equivalent amounts of polybasic acids may be employed. The acid used preferably has a $pK_a$ of not more than 4, advantageously from 1 to 3, especially from 1.5 to 2.5. Strong mineral acids are preferred. Examples of suitable acids are hydrochloric acid, hydrobromic acid, hydriodic acid, sulfuric acid, phosphoric acid, nitric acid, sulfonic acids such as benzenesulfonic acid and p-toluenesulfonic acid, boron-containing acids such as boric acid and fluoboric acid, aliphatic carboxylic acids, eg. chloroacetic acid, dichloroacetic acid, trichloroacetic acid, oxalic acid, o-chlorobenzoic acid and p-chlorobenzoic acid, and mixtures of the above. The acids may be used in a concentrated form, as mixtures with one another and/or advantageously as a mixture with water. Where dilute aqueous acids are used these are advantageously of from 2 to 40% by weight, examples being 2–25% strength by weight hydrochloric acid, 2–25% strength by weight sulfuric acid, 10–40% strength by weight phosphoric acid and 2–10% strength by weight nitric acid. The acidity of the acid should correspond at least to that of 2% strength by weight aqueous sulfuric acid, advantageously of 3–20% strength by weight aqueous sulfuric acid, preferably of 5–10% strength by weight aqueous sulfuric acid, or of 10% strength by weight aqueous phosphoric acid. Hydrochloric acid, p-toluenesulfonic acid, monochloroacetic acid, dichloroacetic acid, trichloroacetic acid, oxalic acid and especially sulfuric acid and phosphoric acid are preferred.

The reaction may be carried out as follows: a mixture of acrolein, acid, water and halohydrocarbon is kept at the reaction temperature for the appropriate reaction time. Advantageously, aqueous acids and the solvent are introduced into the reaction vessel and acrolein or a mixture of acrolein and the solvent is added over a period of, advantageously, from 15 to 150 minutes at the reaction temperature. The reaction time is preferably from 1 to 15 hours, advantageously from 2 to 6 hours. The end product is then isolated from the reaction mixture in a conventional manner, for example by cooling the two-phase reaction mixture, separating off the organic phase and distilling the latter. The aqueous phase is advantageously re-used in a subsequent batch, in place of fresh aqueous acid. If it is envisaged that the reaction is to be carried out in a pressure apparatus, it is also advantageous to introduce the acrolein and halohydrocarbon initially, add the aqueous acid and keep this mixture at the reaction temperature for the time mentioned above.

3-Formyl-5,6-dihydro-2H-pyran, obtainable by the process of the invention, is a valuable starting material for the preparation of dyes and crop protection agents. Concerning the use of the product, reference may be made to the publications cited above.

EXAMPLE 1

(a) 564 g of water, 36 g of sulfuric acid (calculated as 100% strength material) and 400 ml of 1,1,2-trichloroethane were heated to the boil. 125 g of acrolein were added dropwise at 85° C. over 1 hour, with stirring, and the mixture was then refluxed for a further 6 hours at 87° C. The lower, organic phase of the reaction mixture was separated off and the upper phase was extracted once more with 100 ml of trichloroethane. The two organic phases were distilled. 66 g (53% of theory) of 3-formyl-5,6-dihydro-2H-pyran, boiling point 96° C./38 mbar, were obtained. The product was 99.3% pure.

(b) 400 ml of 1,1,2-trichloroethane were added to the aqueous phase and reaction (1a) was repeated with a further 125 g of acrolein. 75 g (60% of theory) of 3-formyl-5,6-dihydro-2H-pyran, boiling point 96° C./38 mbar were obtained. The product was 99.3% pure.

EXAMPLE 2

The procedure described in Example 1 was followed except that 540 g of water and 60 g of sulfuric acid (calculated as 100% strength material) were used. The first reaction (1a) gave 72 g (58% of theory), and the subsequent reaction (1b) 78 g (63% of theory), of 3-formyl-5,6-dihydro-2H-pyran, boiling point 93° C./30 mbar. The product was 99.3% pure.

EXAMPLE 3

The procedure described in Example 1 was followed except that 388 g of water and 212 g of aqueous 85% strength by weight ortho-phosphoric acid were used. The first reaction (1a) 79 g (63% of theory), and the subsequent reaction (1b) gave 91 g (73% of theory), of 3-formyl-5,6-dihydro-2H-pyran, boiling point 93° C./30 mbar. The product was 99.3% pure.

EXAMPLE 4

(a) 560 g of water, 744 g of methylene chloride, 248 g of acrolein and 136 g of aqueous 85% strength by weight ortho-phosphoric acid were kept at 80° C. in an autoclave for 12 hours. The phases were separated and the upper aqueous phase was extracted with 400 ml of methylene chloride. Distillation of the organic phase gave 112 g (45% of theory) of 3-formyl-5,6-dihydro-2H-pyran, boiling point 93° C./30 mbar. The product was 99.3% pure.

(b) The aqueous phase was reacted with 248 g of fresh acrolein and 744 g of methylene chloride, similarly to Example (1a). 131 g (53% of theory) of 3-formyl-5,6-dihydro-2H-pyran, boiling point 93° C./30 mbar, were obtained. The product was 99.3% pure.

EXAMPLE 5

The procedure of Example 3 was followed, but 200 g of acrolein were used. The first reaction (3a) gave 122 g (61% of theory), and the subsequent reaction (3b) 138 g (69% of theory), of 3-formyl-5,6-dihydro-2H-pyran, boiling point 93° C./30 mbar. The product was 99.2% pure.

EXAMPLE 6

The procedure of Example 3 was followed, but using 400 ml of trichloroethylene. The first reaction (3a) gave 76 g (61% of theory), and the subsequent reaction (3b) 80 g (64% of theory), of 3-formyl-5,6-dihydro-2H-pyran, boiling point 93° C./30 mbar. The product was 99.2% pure.

EXAMPLE 7

The procedure of Example 4 was followed, but using 700 ml of 1,1,1-trichloroethane. The first reaction (4a) gave 126 g (51% of theory), and the subsequent reaction (4b) 149 g (60% of theory), of 3-formyl-5,6-dihydro-2H- pyran, boiling point 93° C./30 mbar. The product was 99.2% pure.

EXAMPLE 8

(Comparative Example)

(a) 300 g of water, 100 g of sulfuric acid (calculated as 100% strength material) and 400 ml of toluene were heated to the boil. 100 g of acrolein were added dropwise at 85° C. over 2 hours, with stirring, and the mixture was then refluxed for a further 4 hours at 86° C. The upper, organic phase was separated off and the lower phase was extracted once more with 100 ml of toluene. The two toluene phases were distilled. 30 g (30% of theory) of 3-formyl-5,6-dihydro-2H-pyran, boiling point 95° C./35 mbar, were obtained. The product was 99.2% pure.

(b) 400 ml of fresh toluene were added to the aqueous phase and reaction (1a) was repeated with a further 100 g of acrolein. 45 g (45% of theory) of 3-formyl-5,6-dihydro-2H-pyran, boiling point 96° C./38 mbar were obtained. The product was 99.2% pure.

(c) A third reaction, carried out similarly to (1b), gave no further increase in yield.

We claim:

1. A process for the preparation of 3-formyl-5,6-dihydro-2H-pyran of the formula

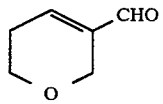

I by conversion of acrolein in the presence of water, acids and organic solvents at an elevated temperature, wherein the reaction is carried out in the presence of halohydrocarbons of 1 to 6 carbon atoms and 1 to 6 halogen atoms as solvents, at between 60° and 150° C.

2. A process as claimed in claim 1, wherein the conversion is carried out at between 60° and 120° C.

3. A process as claimed in claim 1, wherein the conversion is carried out at between 70° and 120° C.

4. A process as claimed in claim 1, wherein the conversion is carried out with from 100 to 1000% by weight of water, based on the weight of acrolein.

5. A process as claimed in claim 1, wherein the conversion is carried out using cycloaliphatic, aromatic or aliphatic halohydrocarbons.

6. A process as claimed in claim 1, wherein the conversion is carried out using amyl chloride, cyclohexyl chloride, dichlorobutanes, isopropyl bromide, n-propyl bromide, butyl bromide, ethyl iodide, propyl iodide, pentachloroethane, 1,1-dichloroethane, n-propyl chloride, 1,2-cis-dichloroethylene, n-butyl chloride, 2-, 3- or iso-butyl chloride, fluorobenzene, bromobenzene, iodobenzene, o-, p- and m-dichlorobenzene, o-, p- and m-dibromobenzene, 1,2,4-trichlorobenzene, 1,4-dibromobutane, chloroform, carbon tetrachloride, 1,1,1,2-tetrachloroethane, 1,1,2,2-tetrachloroethane, 1,1-, 1,2-, 1,3- and 2,2-di-chloropropane, trichloropropane, tetrachloroethylene, chlorobenzene, methylene chloride, 1,2-dichloroethane, 1,1,1- and 1,1,2-trichloroethane, trichloroethylene or mixtures of the above.

7. A process as claimed in claim 1, wherein the conversion is carried out with from 10 to 200% by volume of solvent, based on the volume of water.

8. A process as claimed in claim 1, wherein the conversion is carried out with from 0.01 to 10 equivalents of acid per mole of acrolein.

9. A process as claimed in claim 1, wherein the conversion is carried out with an acid having a pK$_a$ of not more than 4.

* * * * *